United States Patent [19]

Kirwan, Jr.

[11] Patent Number: 5,196,009
[45] Date of Patent: Mar. 23, 1993

[54] NON-STICKING ELECTROSURGICAL DEVICE HAVING NICKEL TIPS

[76] Inventor: Lawrence T. Kirwan, Jr., 203 Indian Pond Rd., Kingston, Mass. 02364

[21] Appl. No.: 757,575

[22] Filed: Sep. 11, 1991

[51] Int. Cl.⁵ .............................................. A61B 17/39
[52] U.S. Cl. ......................................... 606/51; 606/52
[58] Field of Search .................. 606/41, 42, 45, 48–52

[56] References Cited

U.S. PATENT DOCUMENTS

| | | | |
|---|---|---|---|
| 3,685,518 | 8/1972 | Beverle et al. | 606/51 |
| 4,228,800 | 10/1980 | Degler, Jr. et al. | 606/50 X |
| 4,492,231 | 1/1985 | Auth | 606/51 X |
| 4,850,353 | 7/1989 | Stasz et al. | 606/45 X |
| 4,890,610 | 1/1990 | Kirwan, Sr. et al. | 606/51 |
| 5,007,908 | 4/1991 | Rydell | 606/50 X |

Primary Examiner—Lee S. Cohen

[57] ABSTRACT

A non-sticking set of bipolar forceps manufactured by forming the first and second blade portions from nickel.

1 Claim, 1 Drawing Sheet

NON-STICKING ELECTROSURGICAL DEVICE HAVING NICKEL TIPS

BACKGROUND OF THE INVENTION

This invention relates to surgical forceps and more specifically to non-sticking bipolar forceps With the blade portions formed of nickel.

In many of the current commercial embodiments of monopolar and bipolar forceps, the tips of the blade portions frequently adhere to the tissue which they are operating upon. When adherence occurs, it may be required to pull on the tissue to separate the tips of the forceps from the forceps. Such violent separation causes further bleeding and requires frequent cleaning of the tips of the forceps.

In order to avoid adherence of the tips of the blade portions of bipolar forceps to the tissue which they are operating upon the tips may be formed of metals or alloys with large thermal conductivities. The patent to Auth U.S. Pat. No. 4,492,231 discloses that a copper alloy of 2% beryllium, 98% copper plated with nickel to provide chemical inertness and surface hardness. Anodized Niobium electrodes have been used to reduce eschar buildup. Stops may be formed spaced from the tips which as operative pressure is applied to the tips bear against each other causing the tips to spread preventing the mentioned adherence. Note also the patent to Beuerle et al U.S. Pat. No. 3,685,518 which avoids aherence by the design of the forceps tips.

The bipolar forceps disclosed herein are identical with that shown in the U.S. Pat. No. to Kirwan et al 4,890,610 issued Jan. 2, 1990 except that the present bipolar forceps are manufactured by coining unitary first and second blade portions from Nickel 200 manufactured by the International Nickel Company, Inc.

SUMMARY OF THE INVENTION

The invention disclosed herein comprises a set of bipolar forceps manufactured by coining untary first and second blade portions from Nickel 200 manufactured by the International Nickel Company, Inc.

BRIEF DESCRIPTION OF THE DRAWINGS

Further details are explained below with the help of the example(s) illustrated in the attached drawings in which.

DESCRIPTION OF THE PREFERRED EMBODIMENT(S)

Figure 1:
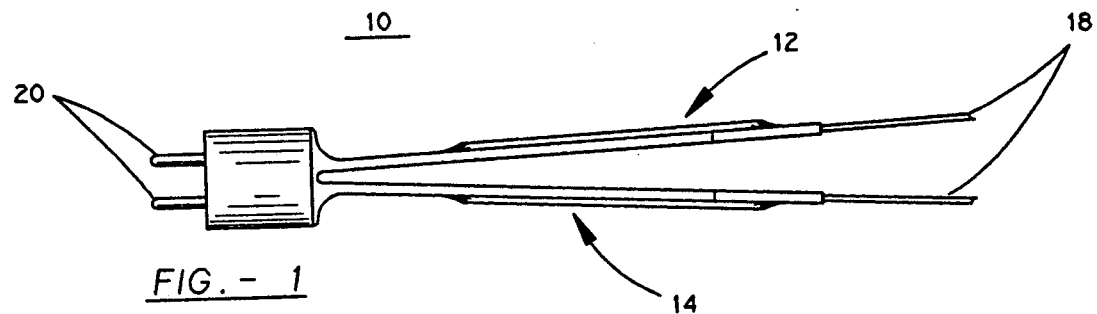
FIG. 1. is a side elevational view of the bipolar forceps according to the present invention.
Figure 2:
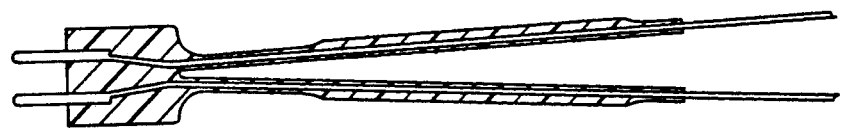
FIG. 2. is a cross section taken through the bipolar forceps taken on line 2—2 of FIG. 1.
Figure 3:
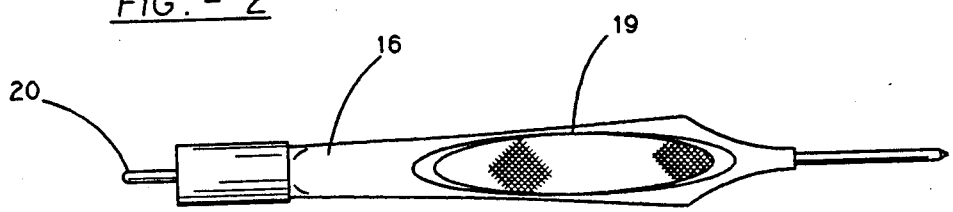
FIG. 3 is a top plan view of the bipolar forceps shown in FIG. 1.
Figure 4:
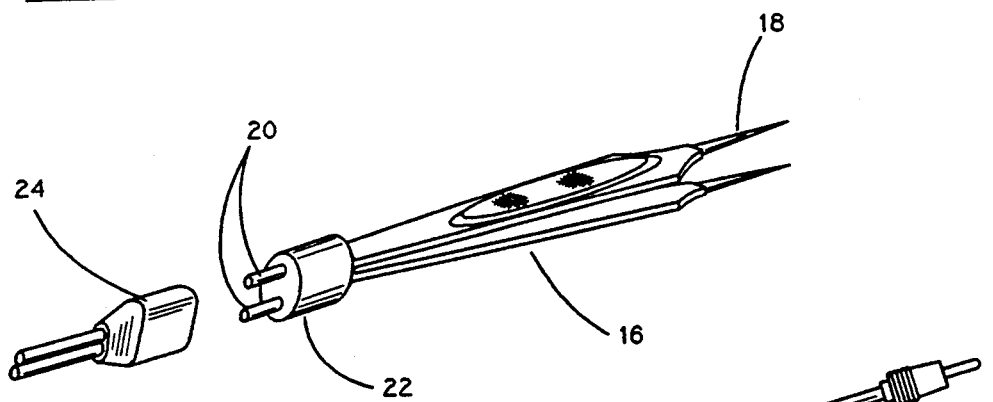
FIG. 4 is a perspective view of the bipolar forceps shown in FIG. 1.

There is shown in the drawings a pair of bipolar forceps 10 comprising a first tine or blade portion 12 and a second blade portion 14.

The bipolar forceps 10 are manufactured by coining the unitary first and unitary second blade portions 12, 14 completely from Nickel 200. Each of them is placed in a mold and overmolded with a plastic of our choice, for example, polystyrene, PDC #11-10 Green PS manufactured by the Dow Chemical Co or PVC product #GA-90990-745-Green manufactured by Gobal Products Corp, forming a coat 16. The plastic leaves a portion of one terminal end of the blade portion exposed to form a tip 18. The plastic should be stable under gamma radiation. If the bipolar forceps 10 is intended to be disposable, then an inexpensive plastic which fits the other requirements should be utilized. Obviously the plastic should have sufficient dielectric strength for the currents and voltages which are normally encountered in bipolar type instruments. The first and second bade portion 12, 14 function as single or in line electrical conductors. A portion of the coat 16 is scribed externally to form a body portion 19 which as shown in cross section provides an arced configuration. Electrically speaking one of the blade portions 12, 14 will carry a positive current while the other carries a negative current. Each of the blade portions 12, 14 has its terminal end remole from the tip 18 formed into a connector pin 20. At the overmolding step the area adjacent the connector pins 20 is formed into a connector portion 22. This Connector portion 22 is configured as an enlarged collar portion. The end result is a unitary bipolar forceps 10 which includes the first and second blade portions 12, 14, having a predetermined area with a coat 16 and a connector portion 22 with the exposed tips 18 and connector pins 20. The first and second blade portions 12, 14 are shown in angular, spaced relation to each other although they may be in spaced, parallel relation to each other if desired. The tips 18 may be straight. They may be bent upwardly first and down slightly to provide a oattation tip. The tips may be bent in other ways if desired.

The bipolar forceps 10 are used for manipulating tissue and at the surgeon's desire coagulating or desiccating the tissue by a voltage from an electrosurgical generator (not shown) connected to the bipolar forceps 10. The electrosurgical generator is connected to the connector pins 20 by an assembly which includes a socket 24 at one end and a pair of banana pin connectors at the other end connected together by a pair of wires. From the each of the banana pin connectors a single wire runs to the keeper 26 and from that point to the socket 24, the single wires are attached and run in paralel. The bipolar forceps are usually sterilized after surgical use. Hot sterilization will cause the plastic coating to melt or deteriorate distorting the first and second tine portions requiring that the bipolar forceps be disposed of.

An acceptable method of sterilization is steam autoclaving. Typically the instruments are wrapped in muslin covers which are placed on the sterilizer unit and then placed inside the sterilizer chamber. When the sterilizer unit is turned on the bipolar forceps will be exposed to steam at 250 degrees F. and pressure for a period of twenty minutes. A variation of the mentioned procedure exposes the instruments to pressure and steam at 270 degrees F. for a period of ten minutes. Both procedures are sufficient to deteriorate the plastic. On sterilization the plastic will melt slightly, causing loss of alignment and dimensions of the first and second tine portions. The plastic itself becomes brittle because of loss of plasticizers. The bipolar forceps are no longer acceptabe for use and must be disposed of.

What I claim is:

1. A microsurgical bipolar forceps comprising elongated, unitary, coined, all nickel first and second blade portions and first and second housing portions, each of the blade portions having first and second terminal ends the first blade portion positioned within the first housing portion and the second blade portion positioned within the second housing portion, the first terminal end providing a tip and the second terminal end providing a connector pin, and the first and second blade portions capable of carrying an electric current, the first housing portion overmolded and covering a major portion of the first blade portion and the second housing portion overmolded and covering a major portion of the second blade portion, the connector pin of each of the blade portions adapted to engage an electrical socket.

* * * * *